United States Patent
Stössel et al.

(10) Patent No.: US 7,179,915 B2
(45) Date of Patent: Feb. 20, 2007

(54) METHOD FOR PRODUCING HIGHLY PURE TRIS-ORTHO METALATED ORGANOIRIDIUM COMPOUNDS

(75) Inventors: Philipp Stössel, Frankfurt (DE); Ingrid Bach, Bad Soden (DE); Hubert Spreitzer, Viernheim (DE); Heinrich Becker, Eppstein-Niederjosbach (DE)

(73) Assignee: Merck Patent GmbH, Darmstadt (DE)

( * ) Notice: Subject to any disclaimer, the term of this patent is extended or adjusted under 35 U.S.C. 154(b) by 60 days.

(21) Appl. No.: 10/515,104

(22) PCT Filed: May 20, 2003

(86) PCT No.: PCT/EP03/05281

§ 371 (c)(1),
(2), (4) Date: Jan. 26, 2005

(87) PCT Pub. No.: WO03/099959

PCT Pub. Date: Dec. 4, 2003

(65) Prior Publication Data

US 2005/0131232 A1    Jun. 16, 2005

(30) Foreign Application Priority Data

May 25, 2002   (DE) ................................. 102 23 337

(51) Int. Cl.
*C07F 5/00*     (2006.01)
*C07D 305/00*   (2006.01)

(52) U.S. Cl. ............... 544/255; 546/2; 549/209; 549/211

(58) Field of Classification Search ............... 544/225; 546/2; 549/209, 211
See application file for complete search history.

(56) References Cited

FOREIGN PATENT DOCUMENTS

| | | |
|---|---|---|
| EP | 1 191 612 A2 | 3/2002 |
| WO | WO 02/02714 A2 | 1/2002 |

OTHER PUBLICATIONS

Grushin, Vladimir V., et al., "New, efficient electroluminescent materials based on organometallic Ir complexes," *Chem. Commun.* :1494-1495 (2001).

*Primary Examiner*—Porfirio Nazario-Gonzalez
(74) *Attorney, Agent, or Firm*—Hamilton, Brook, Smith & Reynolds, P.C.

(57) ABSTRACT

The present invention describes a process for preparing highly pure tris-ortho-metalled organoiridium compounds and pure organometallic compounds of this type, especially compounds of the $d^8$ metals, which may find use as coloring components in the near future as active components (=functional materials) in a series of different types of application which can be classed within the electronics industry in its broadest sense.

20 Claims, No Drawings

METHOD FOR PRODUCING HIGHLY PURE TRIS-ORTHO METALATED ORGANOIRIDIUM COMPOUNDS

RELATED APPLICATIONS

This application is the U.S. National Stage of International Application No. PCT/EP03/05281, which was filed on 20 May 2003, published in German, and claims priority under 35 U.S.C. §119 or 365 to German Application No. 102 23 337.3, filed 25 May 2002.

Organometallic compounds, especially compounds of the $d^8$ metals, will find use as coloring components in the near future as active components (=functional materials) in a series of different types of application which can be classed within the electronics industry in the broadest sense.

The organic electroluminescent devices based on purely organic components (for a general description of the construction, see U.S. Pat. Nos. 4,539,507 and 5,151,629) and their individual components, the organic light-emitting diodes (OLEDs), have already been introduced onto the market, as confirmed by the car radios having organic displays from Pioneer. Further products of this type will shortly be introduced. In spite of this, distinct improvements are still necessary here, in order that these displays provide real competition to the currently market-leading liquid crystal displays (LCDs) or to overtake them.

A development in this direction which has emerged in the last two years is the use of organometallic complexes which exhibit phosphorescence instead of fluorescence [M. A. Baldo, S. Lamansky, P. E. Burrows, M. E. Thompson, S. R. Forrest, Applied Physics Letters, 1999, 75, 4–6].

For theoretical reasons relating to the spin probability, up to four times the energy efficiency and performance efficiency are possible using organometallic compounds. Whether this new development will establish itself firstly depends strongly upon whether corresponding device compositions can be found which can also utilize these advantages (triplet emission=phosphorescence compared to single emission=fluorescence)-in OLEDs. The essential conditions for practical use are in particular a long-operative lifetime, a high stability against thermal stress and a low use and operating voltage, in order to enable mobile applications.

Secondly, there has to be efficient chemical access to the corresponding highly pure metal complexes, in particular to organoiridium compounds. Especially taking into account the cost of iridium, this is of crucial importance for the economic utilization of the compound class specified.

In the literature, several processes have been described for the preparation of tris-ortho-metalated organoiridium compounds. The general access routes, the yields achieved by them and their disadvantages will be laid out briefly hereinbelow using the basic structure of the compound class mentioned, fac-tris[2-(2-pyridinyl)-κN )phenyl-κC]-iridium (III).

Starting from hydrated iridium(III) chloride and 2-phenylpyridine, fac-tris[2-(2-pyridinyl-κN)phenyl-κC]-iridium (III) was obtained in an about 10% yield after a complicated chromatographic purification process [K. A. King, P. J. Spellane, R. J. Watts, J. Am. Chem. Soc., 1985, 107, 1431–1432].

K. Dedeian et al. describe a process starting from iridium (lll) acetylacetonate and 2-phenylpyridine, by which fac-tris [2-(2-pyridinyl-κN)phenyl-κC]-iridium(III) was obtained in a 45% yield. Analogously to the above-described process, it is necessary in this process too to free the product of impurities by chromatographic processes, and in this case, as a result of the solubility behavior, halogenated hydrocarbons are used [K. Dedeian, P. I. Djurovich, F. O. Garces, G. Carlson, R. J. Watts, lnorg. Chem., 1991, 30, 1685–1687].

Different substituted fac-tris[2-(2-pyridinyl)-κN]phenyl-κC]-iridium(III) compounds, for example those having fluorinated ligands, are obtainable by this route only in moderate yields and purities, and in some cases only in very small yields (<20%).

In the nearest prior art, di-μ-chlorotetrakis[2-(2-pyridinyl-κN)phenyl-κC]diiridium(III) which initially has to be prepared in an approx. 72% yield from hydrated iridium(III). chloride and 2-phenylpyridine [S. Spouse, K. A. King, P. J. Spellane, R. J. Watts J. Am. Chem. Soc., 1984, 106, 6647] is used as a reactant. This is then reacted with 2-phenylpyridine and double molar amounts of silver trifluoromethanesulfonate based on the di-μ-chlorotetrakis[2-(2-pyridinyl)-κN]phenyl-κC]di-iridium(III) compound. After chromatographic purification, the authors obtain tris[2-(2-pyridinyl)-κN)phenyl-κC]-iridium(III) in 75% yield [M. G. Colombo, T. C. Brunold, T. Riedener, H. U. Gudel lnorg. Chem., 1994, 33, 545–550]. In addition to the chromatographic purification which is again effected with the aid of halogenated hydrocarbons, the use of double molar amounts of silver trifluoromethanesulfonate based oh the di-μ-chlorotetrakis[2-(2-pyridinyl)-κN)phenyl-κC]-di-iridium(III) is disadvantageous. Remaining traces of silver chloride afford colloidal silver, which makes the thus prepared material less usable for application in OLEDs.

In a fourth literature process, the latter synthetic route is taken directly starting from iridium(III) chloride and the particular, usually fluorinated ligand [S. V. V. Grushin, N. Herron, D. D. LeCloux, W. J. Marschall, V. A. Petrov, Y. Wang, J. Chem. Soc. Chem, Commun. 2001, 1494]. The yields achieved are between 8 and 82% (on average approx. 35%) depending on the substitution on the phenylpyridine ligand. Here too, silver salts, for example $Ag(O_2CCF_3)$, which are expensive and difficult to remove afterward are used in the reaction.

In the table below, these literature data are compared-for a better overview.

TABLE 1

Literature comparison of known preparation processes

| | Reference 1 | Reference 2 | Reference 3 | Reference 4 |
|---|---|---|---|---|
| Reactants | $IrCl_3$ 2-Phenyl-pyridine | $Ir(acac)_3$ 2-Phenyl-pyridine | $[Ir(ppy)_2Cl]_2$ 2-Phenyl-pyridine $AgO_3SCF_3$ | $IrCl_3$ 2-Phenyl-pyridine $AgO_2CCF_3$ |
| Solvent | 2-Ethoxy-ethanol/ water | Ethylene glycol | none | none |
| Temperature | — | 196°–198° C. | 110° C. | 170° C.–195° C. |
| Concentration of iridium reactant | 0.03 mol/l | 0.02 mol/l | no data | no data |
| Molar ratio of iridium reactant to 2-phenyl-pyridine | 1:4 | 1:6.3 | 1:15 | no data |
| Reaction time | 24 h | 10 h | 24 h | 2–9 h |
| Yield | approx. 10% as a by-product of $[Ir(\mu\text{-}Cl)(ppy)_2]_2$ | 45% | 75% | 8–82% (35%) |
| Purity by HPLC | no data | no data | no data | no data |

Reference 1: K. A. King, P. J. Spellane, R. J. Watts, J. Am. Chem. Soc., 1985, 107, 1431–1432.
S. Spouse, K. A. King, P. J. Spellane, R. J. Watts, J. Am. Chem. Soc., 1984, 106, 6647–6653.
Reference 2: K. Dedeian, P. I. Djurovich, F. O. Garces, G. Carlson, R. J. Watts Inorg. Chem., 1991, 30, 1685–1687.
Reference 3: M. G. Colombo, T. C. Brunold, T. Riedener, H. U. Gudel Inorg. Chem., 1994, 33, 545–550.
Reference 4: V. V. Grushin, H. Herron, D. D. Lecloux, W. J. Marshall, V. A. Petrov, Y. Wang, J. Chem. Soc., Chem. Commun. 2001, 1494.

It is thus an object of this invention firstly to provide iridium complexes having a uniform or a mixed ligand set in high purity. It is a further object of the invention to find a process which does not need any complicated purification by means of chromatographic methods. It has now been found that, surprisingly, compounds (I) and (II), according to scheme 1, are obtained starting from iridium(III) halides, anhydrous or as a hydrate, or similar iridium(III) salts, iridium(III) acetonates or similar 1,3-diketo chelate complexes and compounds of the formula (Ib), (IIb), in the presence of Lewis acids (definition: see Jensen, Chem. Rev. 1978, 78, 1), with suitable selection of the reaction parameters such as reaction temperature, concentrations and reaction times, can be obtained reproducibly in from about 90 to 95% yield without the use of chromatographic purification processes, in purities of >99.0% by HPLC (see Example 2 to 8).

This process for the first time provides access to Ir complexes having a mixed ligand set, such as in compound (II), which have purities over >99.0%.

The present invention accordingly provides a process for preparing compounds (I) and (II)

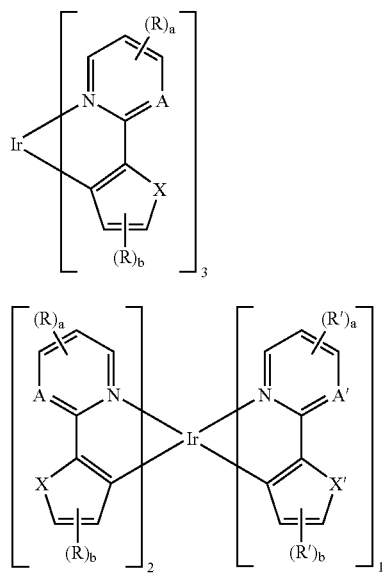

Compound (I)

Compound (II)

where
A, A' are the same or different at each instance and are N or C—H;
X, X' are the same or different at each instance and are —CH=CH—, —CR=CH—, —CR=CR—, N—H, N—$R^1$, O, S or Se; preferably —CH=CH—, —CR=CH— or S;

R, R' is the same or different at each instance and is F, Cl, Br, $NO_2$, CN, a straight-chain or branched or cyclic alkyl or alkoxy group having from 1 to 20 carbon atoms, in which one or more nonadjacent $CH_2$ groups may be replaced by —O—, —S—, —$NR^1$— or —$CONR^2$—, and in which one or more hydrogen atoms may be replaced by F, or an aryl or heteroaryl group having from 4 to 14 carbon atoms which may be substituted by one or more nonaromatic R radicals; and a plurality of R substituents, either on the same ring or on the two different rings, may together in turn form a further mono- or polycyclic ring system;
$R^1$ and $R^2$ are the same or different and are H or an aliphatic or aromatic hydrocarbon radical having from 1 to 20 carbon atoms,
a is 0, 1, 2, 3 or 4, preferably 0 or 1;
b is 0, 1 or 2;
by reacting a compound (Ia), (IIa), (IIIa)

$$IrY_3 \cdot nH_2O \quad (Ia)$$

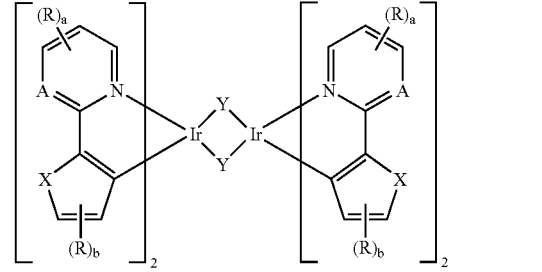

where
Y is F, Cl, Br, OH or a straight-chain or branched or cyclic alkoxy group having from 1 to 8 carbon atoms or a phenoxy group,
$R^3$ and $R^4$ are the same or different at each instance and have the definition of $R^1$ and $R^2$ or $CF_3$;
with a compound (Ib), (IIb)

Compound (Ib)

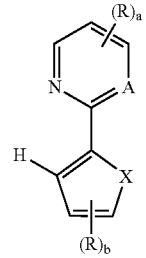

-continued

Compound (IIb)

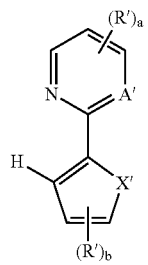

where the A, A', X, X', R, R' radicals, a and b are each as defined above, with addition of a Lewis acid.

The process according to the invention is illustrated by scheme 1.

Scheme 1a:

IrY$_3$·nH$_2$O + 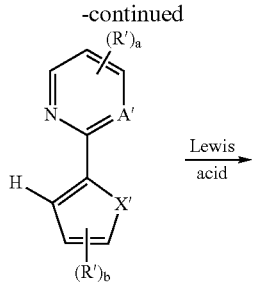 $\xrightarrow{\text{Lewis acid}}$

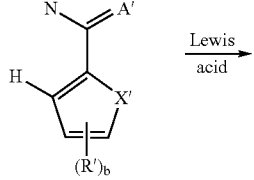

Scheme 1b:

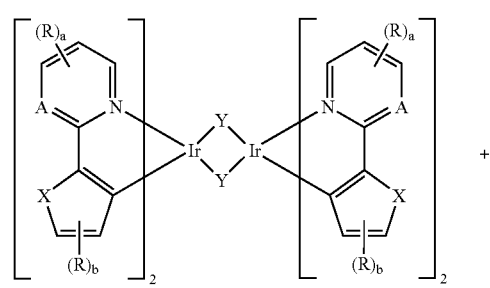

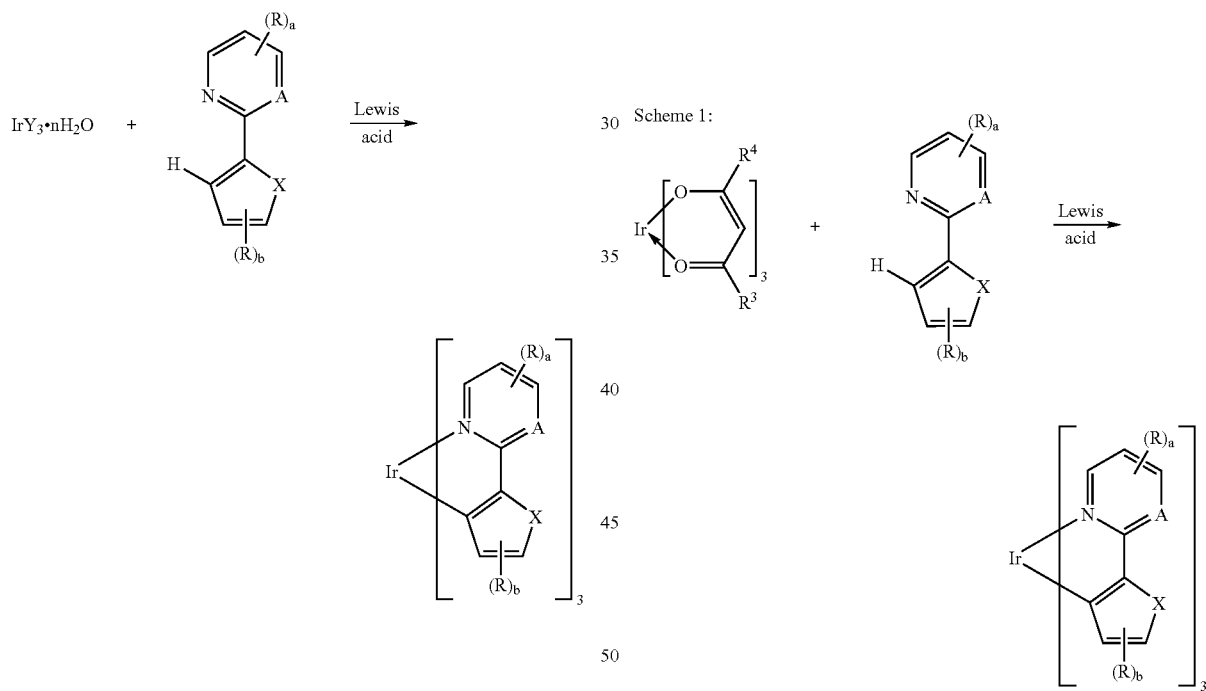

Inventive iridium-containing reactants are iridium halides, anhydrous or a hydrate, for example IrCl$_3$, IrCl$_3$nH$_2$O, IrBr$_3$, IrBr$_3$nH$_2$O, more preferably IrCl$_3$nH$_2$0, or dinuclear iridium complexes of the formula (IIa), for example di-μ-chlorotetrakis[(2-pyridinyl-κN)(phenyl)-κC]diiridium(III), di-μ-chlorotetrakis[(2-pyridinyl-κN)(4',6'-difluorophenyl)-κC]diiridium(III), di-μ-chlorotetrakis[(2-(3-methyl)pyridinyl-κN)(6'-methylphenyl)-κC]diiridium(III), di-μ-chlorotetrakis[(2-(3-trifluoromethyl)pyridinyl-κN (6'-fluorophenyl)-κC]diiridium(III), di-μ-chlorotetrakis[(2-pyridinyl-κC)(4'-fluorophenyl)-κC]diiridium(III), di-μ-chlorotetrakis[(2-pyridinyl-κN)(4'-fluorophenyl)-κC]diiridium (III), di-μ-chloro-tetrakis[(2-(3-trifluoromethyl)pyridinyl- κN)(phenyl)-κC]diiridium(III), di-μ-chlorotetrakis[(2-bis(3, 5-trifluoromethyl)pyridinyl-κN)(phenyl)-κC]diiridium(III) or Ir(III) acetylacetonate.

Preferred Lewis acids are those which contain, as a Lewis-acidic site, an element of the 3rd and/or 4th main group and/or of the 2nd to 10th transition group.

Particularly preferred Lewis acids contain, as an element of the 3rd and/or 4th main group, B, Al or Sn, for example trimethyl borate, triethyl borate, triisopropyl borate, boron trifluoride-ether complex, aluminum(III) fluoride, chloride, .bromide, iodide, butoxide, ethoxide, isopropoxide, phenoxide, tin(II) chloride, bromide, fluoride, iodide, tin(IV) chloride, bromide, fluoride or iodide.

Particularly preferred Lewis acids contain, as an element of the 2nd to 10th transition group, Fe, Zn, Ti or Zr, for example iron(III) chloride, bromide, iodide, iron(II) chloride, bromide, iodide, zinc(II) chloride, bromide, iodide, titanium(IV) or zirconium(IV) chloride, bromide, fluoride, iodide, ethoxide, butoxide, methoxide, chloride triethoxide, chloride triisopropoxide, 2-ethylhexoxide, fluoride.

Explicitly excluded are silver salts, since the iridium complexes prepared therewith contain traces of silver salts or of colloidal silver even after complicated purification, which makes the thus prepared materials less usable for application in OLEDs.

The inventive molar ratio of the Lewis acid to the iridium-containing reactant is from 0.01:1 to 10:1; preference is given to a ratio of from 1:1 to 5:1; particular preference is given to a ratio of from 2:1 to 4:1.

Inventive reaction media are the compounds of the formula (Ib), (IIb) themselves, provided that they are liquid under the reaction conditions, and also high-boiling aprotic or protic solvents, for example decalin, naphthalene, dimethyl sulfoxide, xylene, anisole, ethylene glycol, propylene glycol, triethylene glycol dimethyl ether, poly(ethylene glycol) dimethyl ether or N-methylpyrrolidone (NMP), hydrogen fluoride or supercritical carbon dioxide, more preferably decalin and compounds of the, formula (Ib) and/or (IIb).

According to the invention, the reaction is carried out within a temperature range of from 110° C. to 220° C., preferably within the range from 130° C. to 200° C.

The inventive molar ratio of the iridium-containing reactant of the formula (Ia or IIIa) to the arylpyridine derivative or arylpyrimidine derivative (compounds of the formula (Ib)) is from 1:3 to 1:100; preference is given to a ratio of from 1:5 to 1:50; particular, preference is given to a ratio of from 1:10 to 1:20.

In the case of the synthesis of the compound (II) starting from the dinuclear iridium complexes of the formula (IIa), the ratio of the iridium-containing reactant to the arylpyridine derivative or arylpyrimidine derivative is from 1:1 to 1:100; preference is given to a ratio of from 1:3 to 1:60; particular preference is given to a ratio of from 1:4 to 1:20.

When the concentrations are lower than those mentioned above, the result, in addition to lower conversion, is the formation of by-products, and thus contamination of the product.

According to the invention, the reaction is carried out within from 2 to 120 h, preferably in the range from 5 to 80 h. When the reaction time is below that specified, incomplete conversion of the iridium-containing reactant used has, which leads to yield losses and to contamination of the product.

The compounds of the formula (I) and (II) described in the prior art have hitherto been obtainable in maximum yields of up to 96% or had to be purified by means of complicated chromatographic methods. However, the inventive preparation allows compounds of the formula (I) and (II) to be obtained in purities of more than 99%, preferably of more than 99.9%. Such pure compounds (this is especially true of compounds (II) having a mixed ligand set) were hitherto not known and therefore likewise form part of the subject-after of the present invention. The present invention is illustrated in detail by the examples which follow, without any intention that it be restricted to these examples. It should thus be possible for those skilled in the art in the field of organic synthesis without any further inventive activity to carry out the inventive reactions on further systems as described above.

EXAMPLE 1

Synthesis of Tris-Ortho-Metalated Organoiridium Compounds

The syntheses which follow were carried out up to workup under a dry pure nitrogen atmosphere or pure argon atmosphere using carefully dried solvents. The reactants used were purchased from ALDRICH [decalin, iridium(III) chloride.nH$_2$O, 2-phenylpyridine] and used without further purification, or prepared by literature processes [di-μ-chlorotetrakis[(2-pyridinyl-κN)(phenyl)κC]diiridium(III) and derivatives: J. Sprouse, K. A. King, P. J. Spellane, J. Am. Chem. Soc. 1984, 106, 6647].

Scheme 2: The positions of the substituents were numbered as follows.

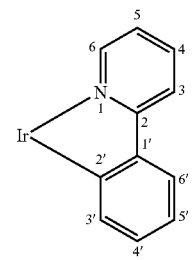

COMPARATIVE EXAMPLE 1

(Analogous to Reference 4, V. V. Grushin, H. Herron D. D. Lecloux, W. J. Marshall, V. A. Petrov, Y. Wang, J. Chem. Soc., Chem. Commun. 2001, 1494)

fac-tris[2'-(2-pyridinyl-κN)-4',6'-difluorophenyl-κC]-iridium(III)

23.72 g (123.8 mmol) of 2-(2,4-difluorophenyl)pyridine were added to 6.07 g (5.0 mmol) of di-μ-chlorotetrakis[(2-pyridinyl-κN)(4',6'-difluorophenyl)-κC]diiridium(III) and 2.42 g (10.8 mmol) of silver trifluoroacetate. The reaction mixture was stirred at 190° C. for 20 h. Subsequently, the reaction mixture was poured onto a mixture of 600 ml of ethanol and 600 ml of 1 N hydrochloric acid. After stirring for 5 minutes, the mixture was filtered with suction through a glass suction filter (P4), and a yellow, finely crystalline precipitate was washed three times with 50 ml of a mixture of ethanol and water (1:1) and three times with 30 ml of ethanol. Finally, the solid was dried at 30° C. in an oil-pump vacuum for 20 h. The yield (at a purity of 90.0–93.4% by NMR) was 5.42–5.75 g, corresponding to 71.2–75.4%.

$^1$H NMR (d$^2$ tetrachloroethane, known hereinbelow as TCE): [ppm]=8.47 (d, $^3J_H$=8.7 Hz, 3H), 7.89 (dd, 3H), 7.65 (dd, 3H), 7.15 (dd, 3H), 6.60 (m,3H), 6.41 (dd, 3H).

EXAMPLE 2 fac-tris[2-(2-pyridinyl-κN)-4',6'-difluorophenyl-κC]-iridium(III)

23.72 g (123.8 mmol) of 2-(2,4-difluorophenyl)pyridine were added to 6.07 g (5.0 mmol) of di-μ-chlorotetrakis[(2-pyridinyl-κN)(4',6'-difluorophenyl)-κC]diiridium(III) and 1.55 g (10.8 mmol) of aluminum(III) chloride. The reaction mixture was stirred at 190° C. for 5 h. Subsequently, the reaction mixture was poured onto a mixture of 600 ml of ethanol and 600 ml of 1N hydrochloric acid. After stirring for 5 minutes, the mixture was filtered with suction through a glass suction filter (P4), and a yellow, finely crystalline precipitate was washed three times with 50 ml of a mixture of ethanol and water (1:1) and three times with 30 ml of ethanol. Finally, the solid was dried at 30° C. in an oil-pump vacuum for 5 h. The yield (at a purity of >99.0% by NMR) was 7.01–7.32 g, corresponding to 91.9–95.9%.

$^1$H NMR (TCE): [ppm] see Example 1

EXAMPLE 3 fac-tris[2-(2-pyridinyl-κN)-4',6'-difluorophenyl-κC]-iridium(III)

23.73 g (123.8 mmol) of 2-(2,4-difluorophenyl)pyridine were added to 6.07 g (5.0 mmol) of di-μ-chlorotetrakis[(2-pyridinyl-κN)(4',6'-difluorophenyl)-κC]diiridium(III) and 1.62 g (11.8 mmol) of zinc (II) chloride. The reaction mixture was stirred at 140° C. for 24 h. See Example 2 for workup. The yield at a purity of >99.0% by NMR was 6.98–7.30 g, corresponding to 91.5–95.7%.

$^1$H NMR (TCE): [ppm] see Example 1.

EXAMPLE 4 bis[(2-pyridinyl-κN)phenyl-κC]mono[2-(2-pyridinyl-κN)(4',6'-difluorophenyl-κC]iridium(III)

23.73 g (123.8 mmol) of 2-(2,4-difluorophenyl)pyridine were added to 5.36 g (5.0 mmol) of di-μ-chlorotetrakis[(2-pyridinyl-κN)phenyl-κC]diiridium(III) and 1.55 g (10.8 mmol) of aluminum(III) chloride. The reaction mixture was stirred at 140° C. for 20 h. See Example 2 for workup. The yield at a purity of >99.0% by NMR was 6.46–6.57 g, corresponding to 93.5–95.3%.

EXAMPLE 5 fac-tris[2-(2-pyridinyl-κN)-4',6'-difluorophenyl-κC] iridium(III)

19.37 g (100 mmol) of 2,4-difluorophenylpyridine were added to 1.52 g (5.0 mmol) of iridium(III) chloride hydrate and 2.66 g (20 mmol) of anhydrous aluminum(III) chloride and stirred at 180° C. for 70 h. See Example 2 for workup. The yield at a purity of >99.0% was 3.59–3.67 g, corresponding to 94.3–96.4%.

$^1$H NMR (TCE): [ppm] see Example 1.

EXAMPLE 6 fac-tris[2-(2-pyridinyl-κN)phenyl-κC]iridium(III)

15.52 g (100 mmol) of phenylpyridine were added to 1.52 g (5.0 mmol) of iridium(III) chloride hydrate and 2.72 g (20 mmol) of anhydrous zinc(II) chloride and stirred at 150° C. for 70 h. See Example 2 for workup. The yield at a purity of 99.0–99.5% was 2.96–3.13 g, corresponding to 90.4–95.8%.

$^1$H NMR (CDCl$_3$): [ppm] 7.84 (m, 3H), 7.58 (m, 6H), 7.48 (m, 3H), 6.82 (m, 6H), 6.69 (m, 6H).

EXAMPLE 7 fac-tris[2-(2-pyridinyl-κN)-4',6 '-difluorophenyl-κC] iridium(III)

3.00 g (15.7 mmol) of 2-(2,4-difluorophenyl)pyridine and 150 ml of decalin were added to 6.07 g (5.0 mmol) of di-μ-chlorotetrakis[(2-pyridinyl-κN)(4',6'-difluoro-phenyl)-κC]diiridium(III) and 1.55 g (10.8 mmol) of aluminum(III) chloride. The reaction mixture was stirred at 180° C. for 48 h. See Example 2 for workup. The yield at a purity of >99.0% was 7.29–7.38 g, corresponding to 95.5–96.8%.

$^1$H NMR (TCE): [ppm] see Example 1.

EXAMPLE 8 fac-tris[2-(2-[pyridinyl-κN)-4',6'-difluorophenyl-κC] iridium(III)

3.00 g (15.7 mmol) of 2-(2,4-difluorophenyl)pyridine and 150 ml of decalin were added to 6.07 g (5.0 mmol) of di-μ-chlorotetrakis[(2-pyridinyl-κN)(4',6'-difluoro-phenyl)-κC]diiridium(III) and 0.15 g (1.1 mmol) of aluminum(III) chloride. The reaction mixture was stirred at 180° C. for 80 h. See Example 2 for workup. The yield at a purity of >99.0% was 7.25–7.41 g, corresponding to 95.1–97.2%.

$^1$H NMR (TCE): [ppm] see Example 1.

What is claimed is:

1. A process for preparing compounds (I) and (II)

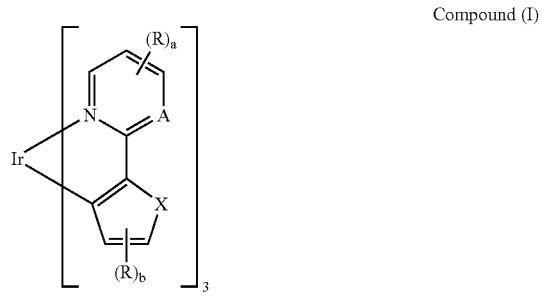

Compound (I)

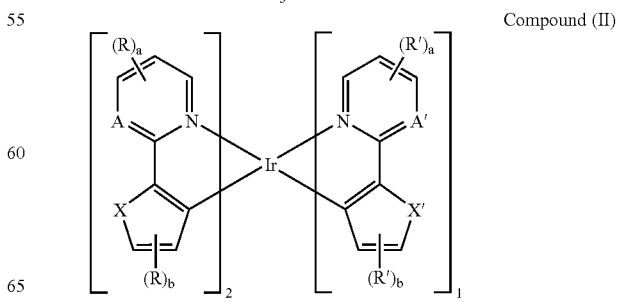

Compound (II)

where
- A and A' are the same or different at each instance and are N or C—H;
- X and X' are the same or different at each instance and are —CH=CH—, —CR=CH—, —CR=CR—, N—H, N—R$^1$, O, S, or Se;
- R and R' are the same or different at each instance and are F, CL, Br, NO$_2$, CN, a straight-chain or branched or cyclic alkyl or alkoxy group having from 1 to 20 carbon atoms in which one or more nonadjacent CH$_2$ groups are optionally replaced by —O—, —S—, —NR$^1$—, or —CONR$^2$— and in which one or more hydrogen atoms are optionally replaced by F, or an aryl or heteroaryl group having from 4 to 14 carbon atoms which are optionally substituted by one or more nonaromatic R radicals, and a plurality of R substituents, either on the same ring or on the two different rings, optionally form a further mono- or polycyclic ring system;
- R$^1$ and R$^2$ are the same or different and are H or an aliphatic or aromatic hydrocarbon radical having from 1 to 20 carbon atoms;
- a is 0,1,2,3, or 4; and
- b is 0,1, or 2;

by reacting a compound (Ia), (IIa), (IIIa)

IrY$_3$·nH$_2$O  (Ia)

(IIa)

(IIIa)

where
- Y is F, Cl, Br, OH, or a straight-chain, branched, or cyclic alkoxy group having from 1 to 8 carbon atoms or a phenoxy group;
- R$^3$ and R$^4$ are the same or different at each instance and have the definition of R$^1$ and R$^2$ or CF$_3$;

with a compound (Ib), (IIb)

Compound (Ib)

Compound (IIb)

where the A, A', X, X', R, R' radicals, a, and b are each as defined above, with addition of a Lewis acid.

2. The process of claim 1, characterized in that X and X' are the same or different at each instance and are —CH=CH—, —CR=CH—, or S.

3. The process of claim 1, characterized in that the iridium-containing reactant used is IrCl$_3$, IrCl$_3$nH$_2$O, IrBr$_3$, IrBr$_3$nH$_2$O, di-μ-chlorotetrakis[(2-pyridinyl-κN)(phenyl)-κC]diiridium(III) and di-μ-chlorotetrakis[(2-pyridinyl-κN)(4',6'-difluorophenyl)-κC]diiridium(lII) and di-μ-chlorotetrakis[(2-(3-methyl)pyridinyl-κN) (6'-methylphenyl)-κC]diiridium(III), di-μ-chlorotetrakis[(2-(3-trifluoromethyl)pyridinyl-κN (6'-fluorophenyl)-κC]diiridium(lII), di-μ-chlorotetrakis[(2-pyridinyl-κN)(4'-fluorophenyl)-κC]diiridium(III), di-μ-chlorotetrakis[(2-(3-trifluoromethyl)pyridinyl-κN) (phenyl)-κC]diiridium(Ill), di-μ-chlorotetrakis[(2-bis(3,5-trifluoromethyl)pyridinyl-κN)(phenyl)-κC]diiridium(III), or Ir(III) acetylacetonate.

4. The process of claim 1, characterized in that the Lewis acid contains, as a Lewis acidic site, an element of the 3$^{rd}$ or 4$^{th}$ main group or of the 2$^{nd}$ to 10$^{th}$ transistion group.

5. The process of claim 4, characterized in that the Lewis acid contains, as a Lewis acidic site, an element of the 3$^{rd}$ or 4$^{th}$ main group.

6. The process of claim 5, characterized in that the Lewis acid contains, at a Lewis acidic site, the elements B, Al, or Sn.

7. The process of claim 5, characterized in that the Lewis acid used is trimethyl borate, triethyl borate, triisopropyl borate, boron trifluoride-ether complex, aluminum (III) fluoride, aluminum (III) chloride, aluminum (III) bromide, aluminum (III) iodide, aluminum (III) butoxide, aluminum (III) ethoxide, aluminum (III) isopropoxide, aluminum (III) phenoxide, tin(II) chloride, tin(II) bromide, tin(II) fluoride, tin(II) iodide, tin(IV) chloride, tin(IV) bromide, tin(IV) fluoride, or tin(IV) iodide.

8. The process of claim 4, characterized in that the Lewis acid contains, as a Lewis-acidic site, an element of the 2$^{nd}$ to 10$^{th}$ transition group.

9. The process of claim 8, characterized in that the Lewis acid contains, as a Lewis-acidic site, the elements Fe, Zn, Ti, or Zr.

10. The process of claim 8, characterized in that the Lewis acid is iron(III) chloride, iron(III) bromide, iron(III) iodide, iron(II) chloride, iron(II) bromide, iron(II) iodide, zinc(II) chloride, zinc(II) bromide, zinc(II) iodide, titanium(IV) or zirconium(IV) chloride, titanium(IV) or zirconium(IV) bromide, titanium(IV) or zirconium(IV) fluoride, titanium(IV) or zirconium(IV) iodide, titanium(IV) or zirconium(IV) ethoxide, titanium(IV) or zirconium(IV) butoxide, titanium (IV) or zirconium(IV) methoxide, chloride triethoxide, chloride triisopropoxide, 2-ethylhexoxide, or fluoride.

11. The process of claim 1, characterized in that mixtures of Lewis acids are used.

12. The process of claim 1, characterized in that the Lewis acid is used in a ratio to the iridium-containing reactant of from 0.01:1 to 10:1.

13. The process of claim 1, characterized in that the ratio of an iridium containing reactant, compounds of the formula (Ia, IIa, IIIa) and ligand of the formula(Ib, IIb) is from 1:1 to 1:100.

14. The process of claim 1, characterized in that the solvent used in decalin, naphthalene, dimethyl sulfoxide, xylene, anisole, ethylene glycol, propylene glycol, triethylene glycol dimethyl ether, poly(ethylene glycol) dimethyl ether or N-methylpyrrolidone (NMP), hydrogen fluoride, or supercritical carbon dioxide.

15. The process of claim 1, characterized in that the reaction is carried out within a temperature range of from 110° C. to 220° C.

16. The process of claim 15, characterized in that the reaction is carried out within a temperature range of from 130° C. to 200° C.

17. The process of claim 1, characterized in that the reaction is carried out within from 5 to 80 h.

18. The process of claim 1, characterized in that:
the iridium-containing reactant used is $TrCl_3$, $IrCl_3nH_2O$, $IrBr_3$, $IrBr_3nH_2O$, di-μ-chlorotetrakis[(2-pyridinyl-κN)(phenyl)-κC]diiridium(III), di-μ-chlorotetrakis[(2-pyridinyl-κN)(4',6'-difluorophenyl)-κC]diiridium(III) and di-μ-chlorotetrakis[(2-(3-methyl)pyridinyl-κN)(6'-methylphenyl)-κC]diiridium(III), di-μ-chlorotetrakis[(2-(3-trifluoromethyl)pyridinyl-κN(6'-fluorophenyl)-κC]diiridium(III), di-μ-chlorotetrakis[(2-pyridinyl-κN)(4'-fluorophenyl)-κC]diiridium(III), di-μ-chlorotetrakis[(2-(3-trifluoromethyl)pyridinyl-κN) (phenyl)-κC] diiridium(III), di-μ-chlorotetrakis[(2-bis(3,5-trifluoromethyl)pyridinyl-κN)(phenyl)-κC]diiridium (III), or Ir(III) acetylacetonate;
the Lewis acid contains, as a Lewis acidic site, an element of the $3^{rd}$ or $4^{th}$ main group or of the $2^{nd}$ to $10^{th}$ transistion group;
the ratio of an iridium containing reactant, compounds of the formula (Ia, IIa, IIIa) and ligand of the formula (Ib, IIb) is from 1:1 to 1:100; and
the solvent used in decalin, naphthalene, dimethyl sulfoxide, xylene, anisole, ethylene glycol, propylene glycol, triethylene glycol dimethyl ether, poly(ethylene glycol) dimethyl ether or N-methylpyrrolidone (NMP), hydrogen fluoride, or supercritical carbon dioxide.

19. A compound of the formula (I)

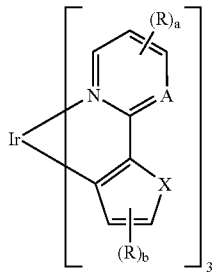

where
A is N;
X is N—H, N—$R^1$, O, S, or Se;
R is the same or different at each instance and is F, Cl, Br, $NO_2$, CN, a straight-chain, branched, or cyclic alkyl or alkoxy group having from 1 to 20 carbon atoms in which one or more nonadjacent $CH_2$ groups are optionally replaced by —O—, —S—, —$NR^1$—, or —$CONR^2$— and in which one or more hydrogen atoms are optionally replaced by F, or an aryl or heteroaryl group having from 4 to 14 carbon atoms which are optionally substituted by one or more nonaromatic R radicals, and a plurality of R substituents, either on the same ring or on the two different rings, optionally form a further mono- or polycyclic ring system;
$R^1$ and $R^2$ are the same or different and are H or an aliphatic or aromatic hydrocarbon radical having from 1 to 20 carbon atoms;
a is 0,1,2,3, or 4; and
b is 0,1, or 2;
whose purity is more than 99.0%.

20. A compound of the formula (II)

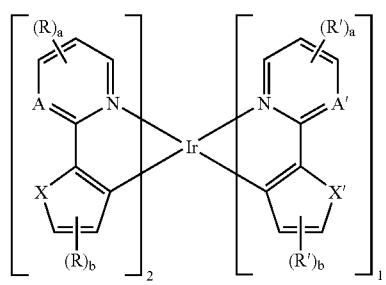

where
A and A' are the same or different at each instance and are CH or N;
X and X' are the same or different at each instance and are N—H, N—$R^1$, O, S, or Se;
R and R' are the same or different at each instance and are F, a straight-chain or branched or cyclic alkyl group having from 1 to 20 carbon atoms in which one or more hydrogen atoms are optionally replaced by F, or an aryl group having from 6 to 14 carbon atoms which are optionally substituted by one or more nonaromatic R' radicals, and a plurality of R substituents, either on the same ring or on the two different rings optionally form a further mono- or polycyclic ring system;
$R^1$ is the same or different and is H or an aliphatic or aromatic hydrocarbon radical having from 1 to 20 carbon atoms,
a is 0,1,2,3, or 4; and
b is 0,1, or 2;
whose purity is more than 99.0%.

* * * * *